United States Patent [19]

Volk

[11] Patent Number: 4,682,866
[45] Date of Patent: Jul. 28, 1987

[54] HEAD-BORNE BINOCULAR INDIRECT OPHTHALMOSCOPE WITH INTEGRATED TELESCOPE

[76] Inventor: David Volk, 3336 Kersdale Rd., Pepper Pike, Ohio 44124

[21] Appl. No.: 669,345

[22] Filed: Nov. 8, 1984

[51] Int. Cl.⁴ .............................................. A61B 3/10
[52] U.S. Cl. ................................................... 351/205
[58] Field of Search ............... 351/205, 216, 217, 218; 350/516

[56] References Cited

U.S. PATENT DOCUMENTS

| | | | |
|---|---|---|---|
| 3,475,082 | 10/1969 | Strietzel | 351/205 |
| 3,582,191 | 6/1971 | Cohen et al. | 351/205 |
| 3,963,329 | 6/1976 | Stumpf et al. | 351/205 |
| 4,056,310 | 11/1977 | Shimizu | 351/205 |
| 4,449,797 | 5/1984 | Kocher et al. | 351/205 |

Primary Examiner—Rodney B. Bovernick
Attorney, Agent, or Firm—Baldwin, Egan & Fetzer

[57] ABSTRACT

There is presented an improved head-borne binocular indirect ophthalmoscope for viewing the aerial image of the fundus of the eye, having the unique feature that it incorporates within each of its two observing portions a two-lens telescope of low magnifying power which magnifies said aerial image of the fundus. The telescope incorporated into the ophthalmoscope differs from the usual coaxial type in that the optical axis of the high powered objective lens and that of the high powered ocular lens of said telescope are caused to intersect each other at an angle of about 94° at the surface of a laterally positioned oblique front surface mirror, said lenses and said mirror being in a fixed relationship to each other within a transversely movable mounting as a fixed telescope unit such that the reflected secondary focus of the objective lens falls at the primary focus of the ocular lens, said unit being attached to a slide which is transversely movable along ways toward and away from a medially positioned oblique front surface mirror whereby adjustments can be made within the ophthalmoscope to accommodate the interpupillary distance of the observer without affecting the relative position of the elements of said telescope unit.

13 Claims, 12 Drawing Figures

PRIOR ART

HEAD-BORNE BINOCULAR INDIRECT OPHTHALMOSCOPE WITH INTEGRATED TELESCOPE

Head-borne binocular indirect ophthalmoscopes presently commercially available subserve two functions: (1) They provide a light source which, in conjunction with a hand-held indirect ophthalmoscopy condensing lens, illuminates the interior of the eye, and (2) they provide a binocular viewing system of the aerial image of the fundus of the eye produced by said condensing lens, said aerial image being an inverted real image formed of light emerging from the eye and refracted by said condensing lens.

PRIOR ART

Monocular indirect ophthalmoscopy utilizing a separate light source to one side and at a distance behind the subject and utilizing a head-borne mirror with a central aperture in front of the examiner's eye and a hand-held +13.00 diopter spherical condensing and image forming lens, was first used in the mid 19th century. By the early 20th century, Gullstrand had designed a large table-model binocular indirect ophthalmoscope. The large size and complexity of the Gullstrand apparatus as well as the inability of the examiner to view the periphery of the retina with it prevented its wide acceptance.

In 1947 Dr. Charles Schepens developed a small head-borne binocular indirect ophthalmoscope incorporating a high intensity illuminating system and two pairs of oblique mirrors for directing the light rays from the aerial image of the fundus to each eye of the examiner. Said aerial image is formed by a hand-held condensing and image forming indirect ophthalmoscopy lens, said lens being separate and distinct from the head-borne indirect ophthalmoscope. The power of the indirect ophthalmoscopy lens may be varied to suit the examiner and its tilt and position may be modified to enhance the viewing of the fundus of the eye. The Schepens head-borne binocular indirect ophthalmoscope greatly increased the ability of the examiner to observe details of the fundus, especially the peripheral portions.

Since Schepens introduced his binocular head-borne indirect ophthalmoscope, several other similar head-borne ophthalmoscopes identical in principle to the Schepens instrument have become commercially available. The inverted aerial image of the fundus when viewed by means of the Schepens ophthalmoscope and similar ophthalmoscopes remains inverted and essentially not magnified. In learning to use the head-borne binocular indirect ophthalmoscope, the examiner must take into account the fact that the image he is observing is inverted and diametrically opposed to the actual position of points in the fundus. Also, when the hand-held indirect ophthalmoscopy lens is of strong dioptric power, the aerial image of the fundus is less magnified although the area of the fundus included in the aerial image is increased.

BRIEF DESCRIPTION OF PREFERRED EMBODIMENTS

Briefly, this invention relates to a new and improved head-borne binocular indirect ophthalmoscope for viewing the aerial image of the fundus of the eye, having the unique feature that it incorporates within each of its two observing portions a two-lens telescope of low magnifying power which magnifies said aerial image of the fundus. The telescope incoprated into the ophthalmoscope differs from the usual coaxial type in that the optical axis of the high powered objective lens and that of the high powered ocular lens of said telescope are caused to intersect each other at an angle of about 94° at the surface of a laterally positioned oblique front surface mirror, said lenses and said mirror being in a fixed relationship to each other within a transversely movable mounting as a fixed telescope unit such that the reflected secondary focus of the objective lens falls at the primary focus of the ocular lens, said unit being attached to a slide which is transversely movable along ways toward and away from a medially positioned oblique front surface mirror whereby adjustments can be made within the ophthalmoscope to accommodate the interpupillary distance of the observer without affecting the relative position of the elements of said telescope unit. A single low-powered columnating lens whose primary focus is at the usual working distance in performing indirect ophthalmoscopy, is fixed in position in front of both of the medially positioned oblique mirrors. Since the telescope and mirror unit is a fixed unit and since the light reflected from said medially positioned oblique mirror and incident upon said telescope objective lens of said unit is columnated, movement of said unit toward and away from said medially positioned oblique mirror along the direction of the incident columnated light rays requires no relative adjustment of said telescope when it is moved transversely to accommodate the observer's interpupillary distance. The incorporation of aberration correcting aspherical objective and ocular lenses within said unit of the indirect ophthalmoscope of this invention and the use of the columnating lens provides to the observer viewing the aerial image of the fundus binocularly a magnified, stereoscopic clear image of the aerial image of the fundus of the eye.

Two types of telescopes are used in this invention: a Galilean telescope wherein the objective lens is of strong positive power and wherein the ocular lens is of strong negative power and the image is seen as clear, enlarged, and inverted, and; an astronomical telescope wherein the objective lens is of strong positive power and the ocular lens is of strong positive power and the image is reinverted and is seen as clear, enlarged, and upright.

BRIEF DESCRIPTION OF THE DRAWINGS

FIG. 8, drawn to scale, is an enlarged detailed view of the arrangement of the front surface mirrors and the included Galilean telescope of the left half of the binocular indirect ophthalmoscope of this invention as shown in FIG. 6 showing the columnating lens, front surface mirrors, and the included positive objective and negative ocular lenses of said Galilean telescope in their respective positions affixed to the housing of the lateral front surface mirror. Also included in FIG. 8 in its proper position for viewing, is a drawing of a section through the eye of the observer.

FIG. 9, drawn to scale, is an enlarged detailed view of the arrangement of the front surface mirrors and the included astronomical telescope of the left half of the binocular indirect ophthalmoscope of this invention analogous to FIG. 8 showing the columnating lens, front surface mirrors, and the included positive objective and positive ocular lenses of said astronomical telescope in their respective positions affixed to the housing of the lateral oblique front surface mirror. Also included in FIG. 9 in its proper position for viewing is a drawing of a section through the eye of the observer.

FIG. 10 is an exploded perspective view of the head-borne ophthalmoscope of this invention showing the apparatus for mounting on the head of the user.

FIG. 10A is a perspective view showing the slide assembly for the lateral front surface mirrors; and, FIG. 11 is a perspective view of the ophthalmoscope of this invention shown mounted on the head of the user.

Figure 1:
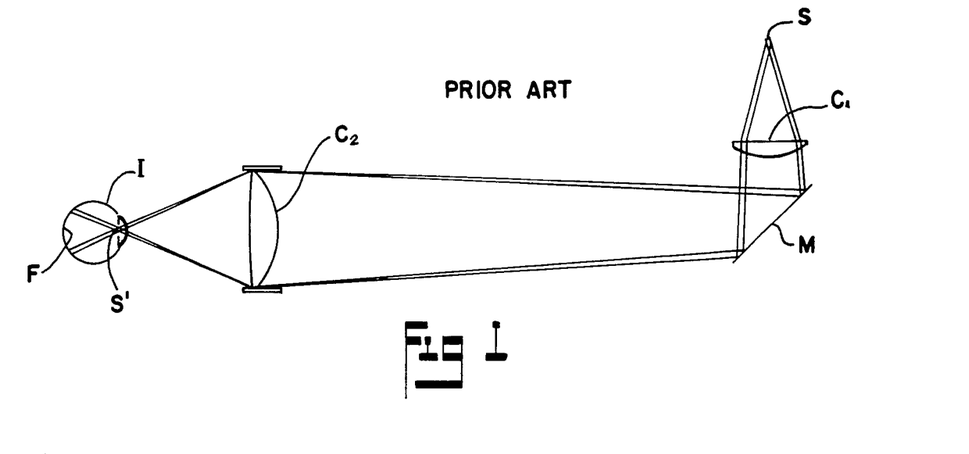
FIG. 1 is a schematic representation of the illuminating system for illuminating the fundus of the eye utilizing the hand-held indirect ophthalmoscopy lens as a condensing lens.
Figure 2:
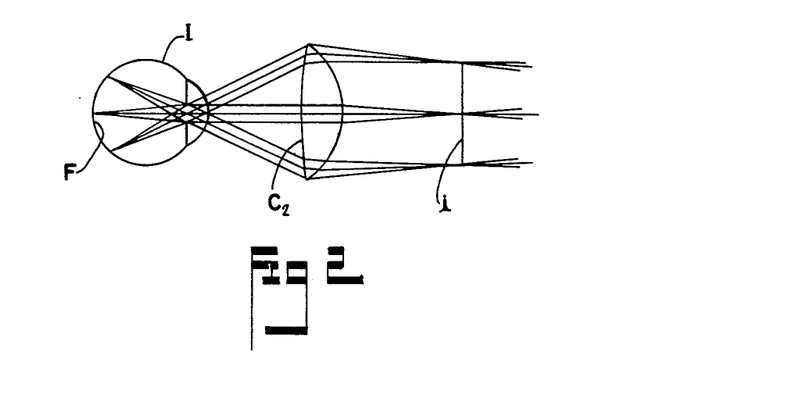
FIG. 2 is a schematic representation of the formation of the inverted aerial image of the fundus of the eye by the hand-held indirect ophthalmoscopy lens.
Figure 3:
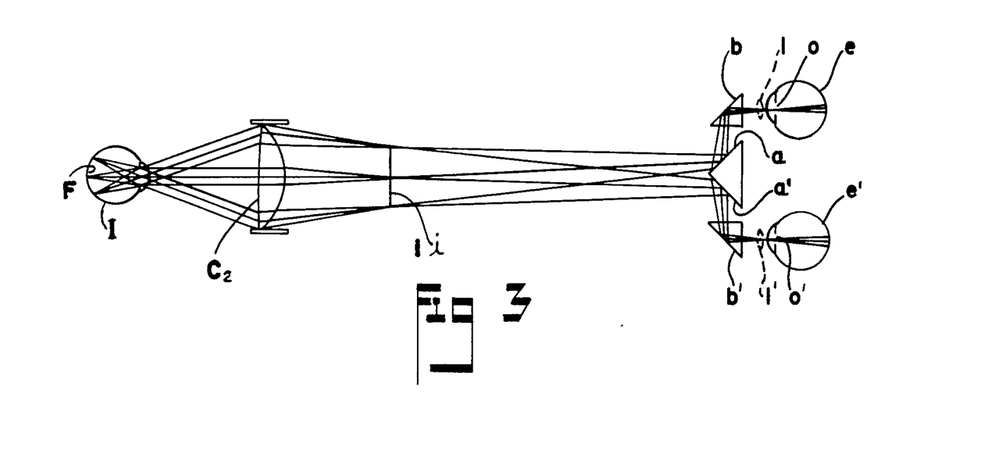
FIG. 3 is a schematic representation of the formation of the inverted aerial image of the fundus of the eye and the binocular indirect ophthalmoscope of the prior art for viewing said inverted aerial image.

In FIG. 1, I have shown schematically the optical system for illuminating the fundus of the eye. Light source S sends light to condensing lens $C_1$ which in turn directs divergent light rays to oblique mirror M which redirects the divergent beam of light to indirect ophthalmoscopy condensing lens $C_2$, which converges the beam of light to form a real inverted image S' of light source S in the vicinity of the center of the pupil of the eye, I. The light rays then diverge to illuminate the fundus F. In FIG. 2 I have shown schematically light rays emerging from the illuminated eye I from points in the fundus F and passing through the pupil of the eye, to be incident upon the back surface of indirect ophthalmoscopy condensing lens $C_2$ and refracted through lens $C_2$ to form a real inverted aerial image i of the fundus F. Since the object points in the fundus are at different depths, aerial image i likewise has depth. The light rays from each point in the fundus passing through image i then continue to the head-borne binocular ophthalmoscope (see FIG. 3) where they impinge upon medial oblique mirrors a and a' and after reflection, upon lateral oblique mirrors b and b' which then direct the reflected light rays to the pupils o and o' of the observer's eyes e and e'. Oblique mirrors b and b' are adjustable towards or away from each other by means of slides and ways not shown in FIG. 3, to match the interpupillary distance of the observer. The observer is thus observing binocularly and stereoscopically inverted aerial image i. Since aerial image i is at a fairly close distance from the observer's eyes, it may be necessary to provide supplementary lenses 1 of about two diopters power in front of the observer's eyes should the observer be presbyopic. The image seen by the observer is inverted and not enlarged, except for slight magnification which results from said two diopter lenses when used.

Figure 4:
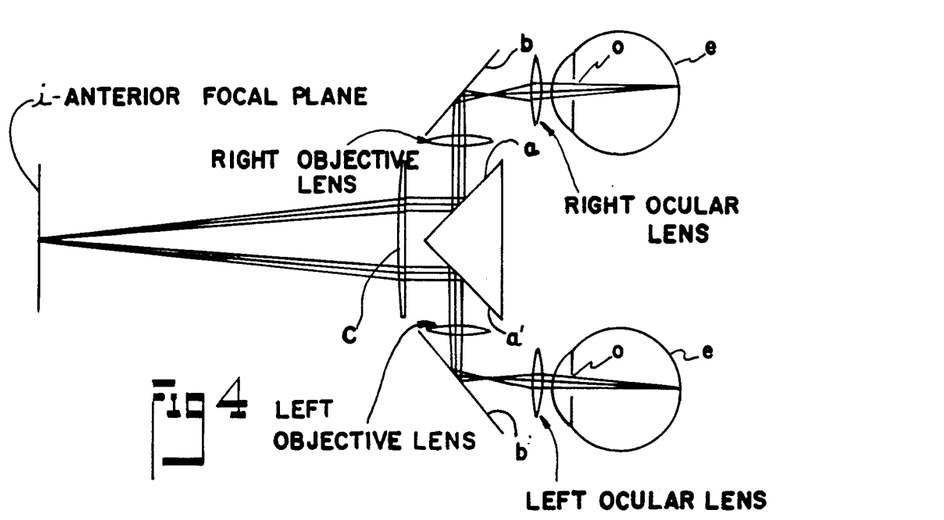
FIG. 4 is a schematic drawing of a section through one embodiment of the binocular indirect ophthalmoscope of this invention showing the columnating lens and the positive objective and positive ocular lenses of the included astronomical telescope.
Figures 4, 5:
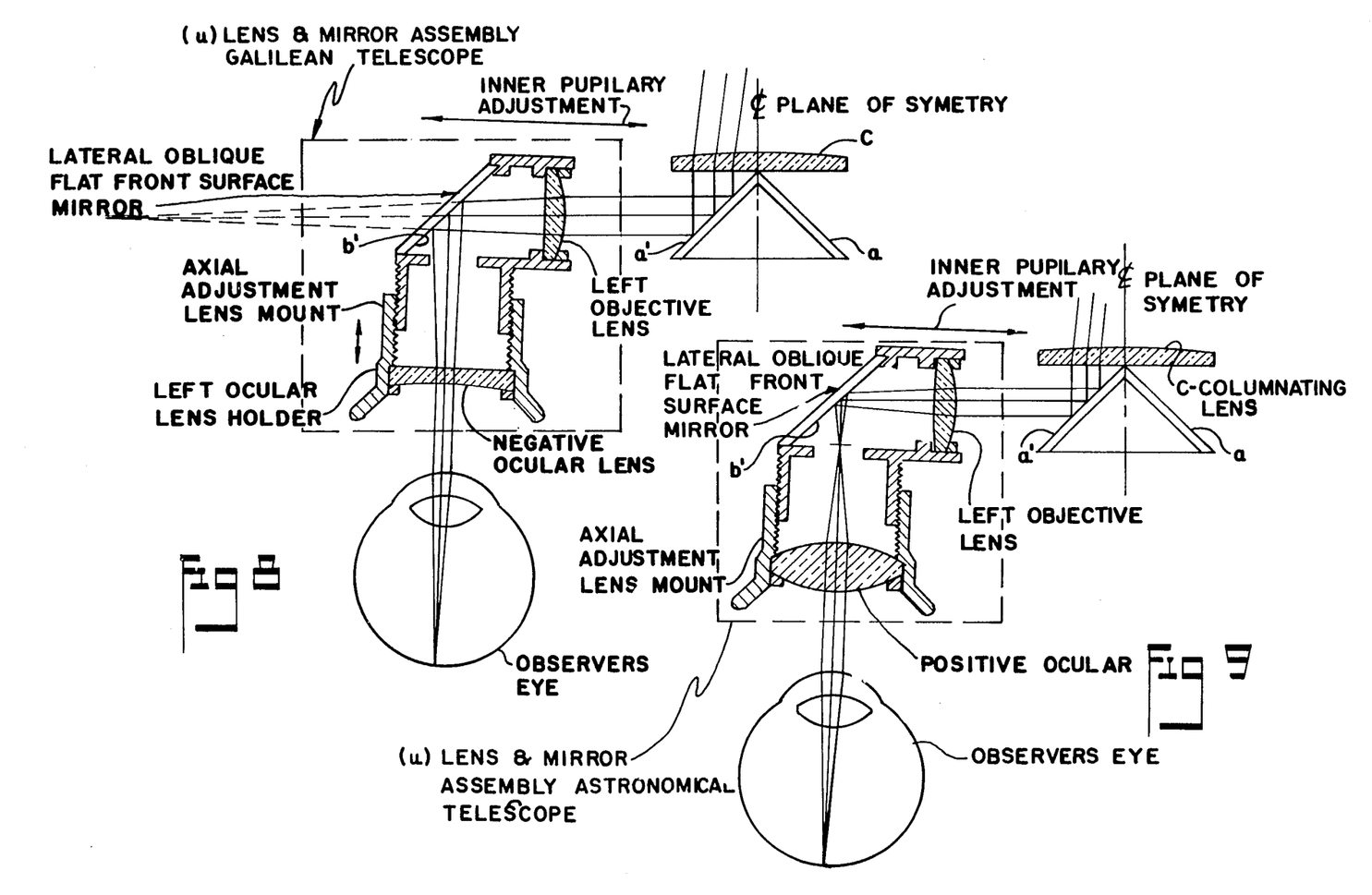
FIG. 5 is a graph of the dioptric power of the columnating lens versus magnification of the aerial image produced by the columnating lens.
Figure 5:
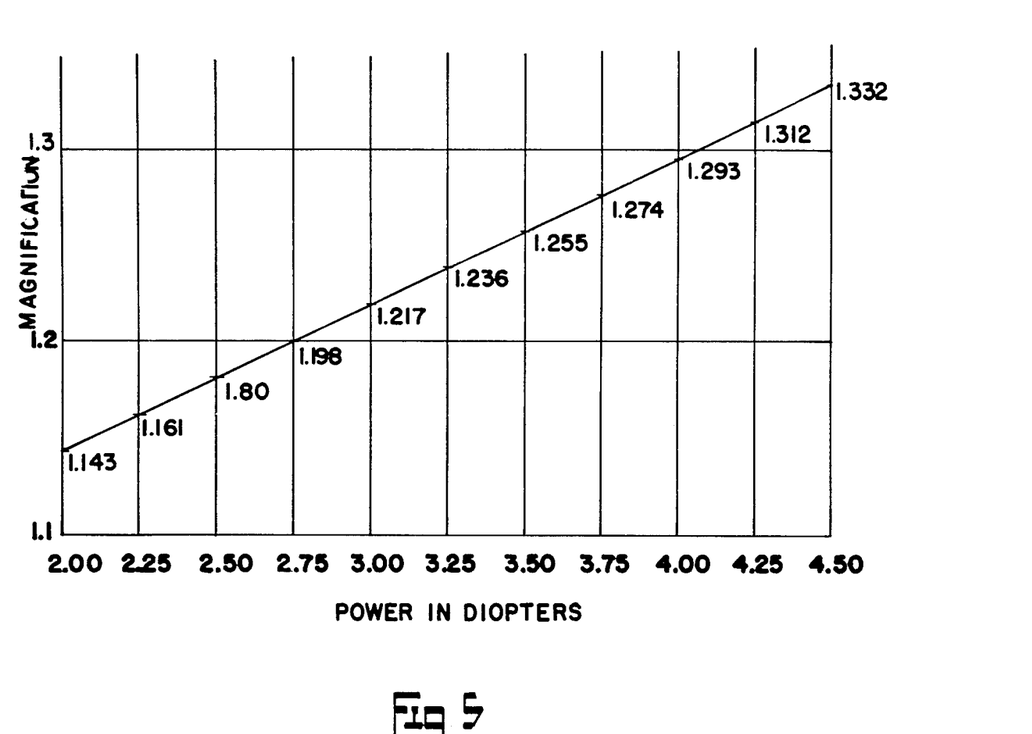

In the present invention, I have improved upon the prior art in two ways, (1) by utilizing a columnating lens c, centered in front of medial oblique mirrors a and a' (see FIG. 4) so that light rays in each bundle from each point in image i, after refaction by said columnating lens, proceed as a homocentric bundle of essentially parallel light rays toward oblique mirrors a and a'. In FIG. 4, I have shown divergent light rays from a central point in image i incident upon columnating lens C and refracted to a homocentric bundle of parallel light rays to each medial oblique mirror a and a'. Since image i has depth, the light rays in the homocentric bundle may be parallel or may be very slightly convergent or divergent. The power of the columnating lens is such that the aerial image i of the fundus lies at its anterior focal plane. I have determined that an anterior vertex power of 3.37 diopters for the anterior focal distance of 29.674 centimeters for the columnating lens, representing the distance between the aerial image i and said columnating lens, is satisfactory. In the actual practice of indirect ophthalmoscopy with a 20 diopter hand-held indirect ophthalmoscopy lens and the 3.37 diopter columnating lens, the distance between the hand-held indirect ophthalmoscopy lens and the observer's eyes would be approximately 16 inches, which is a convenient and comfortable working distance. However, different observers may prefer working distances less than or greater than 16 inches, requiring columnating lenses stronger or weaker than 3.37 diopters respectively. The columnating lens, in addition to its effect with respect to the working distance of the observer, also has the effect of magnifying the aerial image, the stronger its power, the greater the magnification. FIG. 5 is a graph of power of the columnating lens versus its magnification within a range of 1.143 to 1.332. The power of the columnating lens is seen to be in the range of 2.00 to 4.50 diopters and depends upon the preferred working distance of the observer, the stronger lens being used for shorter working distances. Working distance is the distance between the observer's eyes and the hand-held indirect ophthalmoscopy lens. Note that at a power of 3.37 diopters, magnification of the columnating lens is approximately 1.25.

Although FIG. 5 shows columnating lens dioptric powers from 2.00 to 4.50, said lens with powers of less than 2.00 diopters, for example 1.0 diopter, or greater than 4.50 diopters, for example 5.50 diopters, may be used.

A second improvement upon the prior art is the incorporation of a pair of two-lens telescopes of low magnifying power within the indirect ophthalmoscope of this invention.

Figure 6:
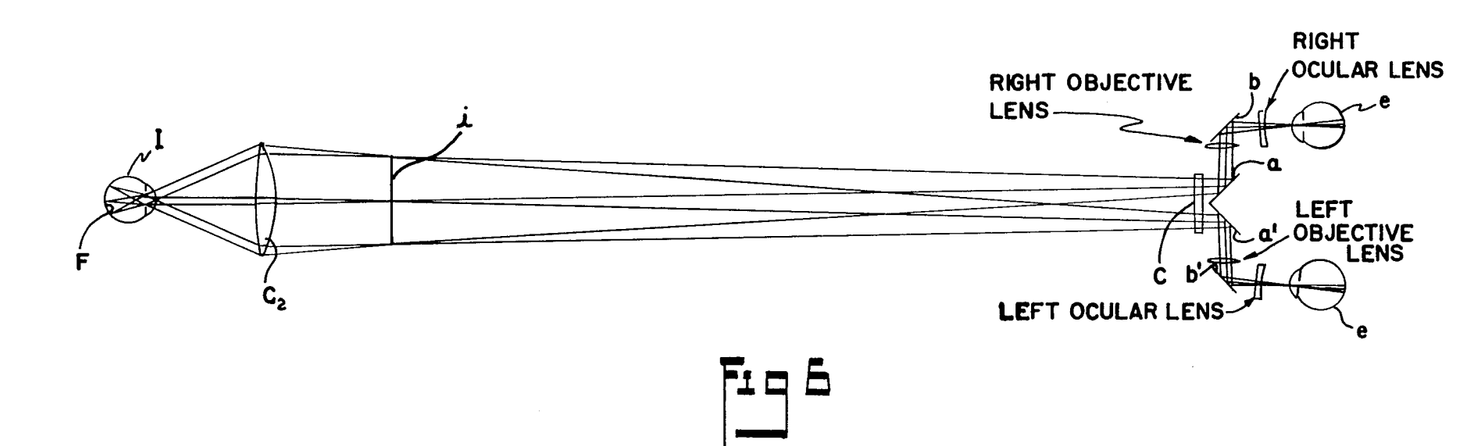
FIG. 6 is a partial schematic drawing to scale of a section through another embodiment of the binocular indirect ophthalmoscope of this invention showing the columnating lens and the positive objectives with negative ocular lenses of the included Galilean telescope.

FIG. 6, drawn to scale, is a schematic representation of the entire optical system of indirect ophthalmoscopy according to this invention from the formation of the aerial image of the illuminated fundus by means of the hand-held indirect ophthalmoscope of this invention which includes firstly the novel single element columnating lens c' and secondly the novel pair of two-element Galilean telescopes each element of which is inclined and fixed in position with respect to its respective lateral oblique flat front surface mirror and each telescope and said lateral oblique mirror comprising a unit u within the direct ophthalmoscope of this invention. Also shown in FIG. 6 is the position and convergence of the observer's eyes. Said telescope units are designed and angled such that the optical axis of each ocular lens is directed toward the center of the apparent position of the aerial image of the fundus.

Figure 7:
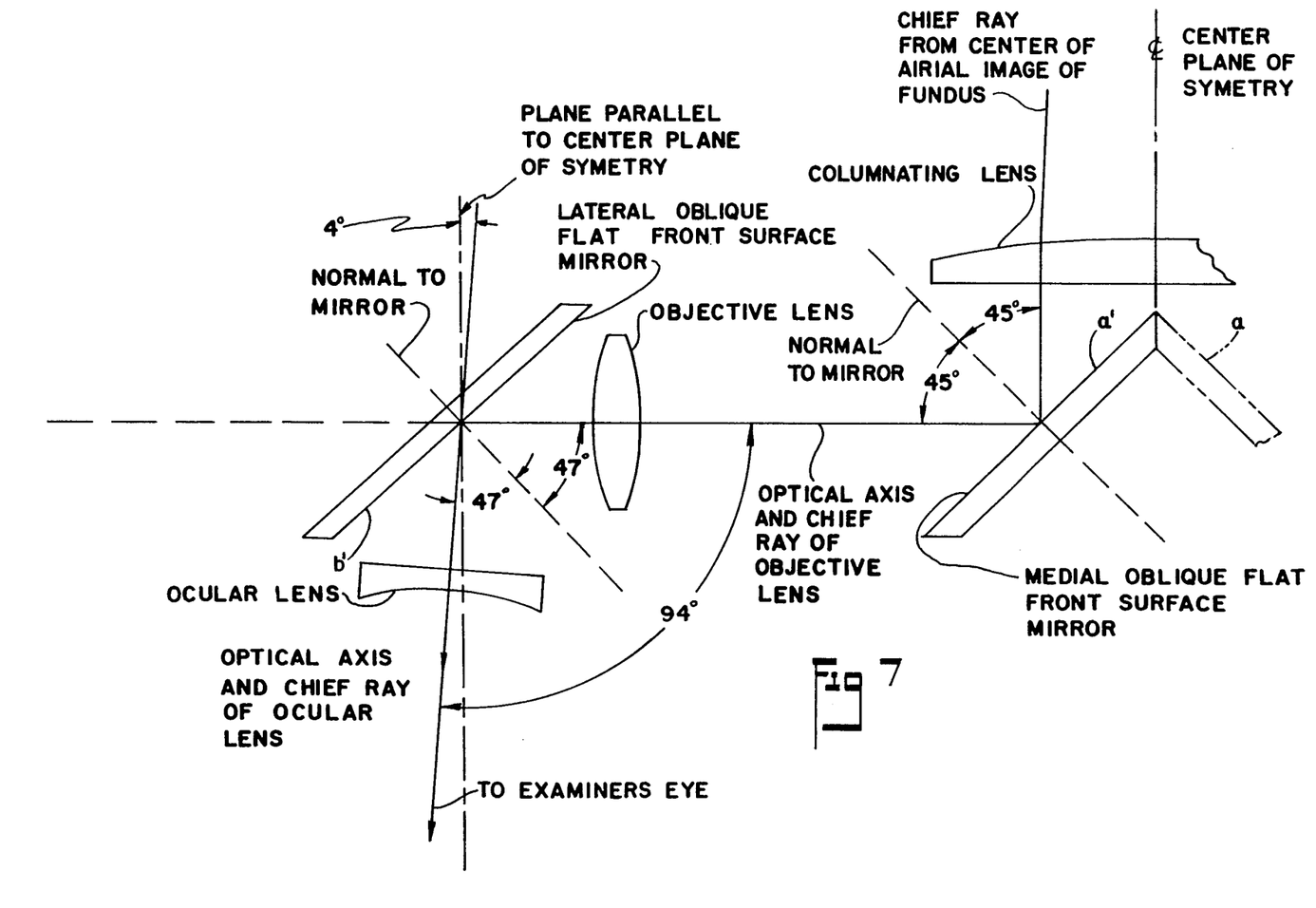
FIG. 7 is a schematic drawing of a portion of the indirect ophthalmoscope of this invention showing the positions and angular relationships of the essential components of the ophthalmoscope.

In FIG. 7, I have shown in greater detail the positions and angular relationships of the mirrors and lenses depicted in the lefthand portion of FIG. 6 along with the path of the axial chief ray which coincides with the optical axis of the telescope of said fixed unit.

The angle between the two medial oblique front surface mirrors a and a' is 90° so that each mirror makes an angle of 45° with respect to the center plane of symmetry of the right and left halves of the indirect ophthalmoscope of this invention. From a point at the center of the aerial image of the fundus which is at the primary focus of the columnating lens, light rays proceed as a homocentric bundle of divergent rays to said columnating lens and are refracted as a homocentric bundle of columnated light rays parallel to said center plane of symmetry, to then intersect the medial oblique mirror at an angle of incidence of 45° and are then reflected at an angle of reflection of 45°. The reflected homocentric bundle of parallel light rays are thus perpendicular to said columnated light rays to be incident upon the objective lens of the telescope of the indirect ophthalmoscope of this invention. The optical axis of said objective lens is parallel to said homocentric bundle of reflected parallel incident light rays and that light ray coinciding with the optical axis of said objective lens is the axial chief ray which proceeds through said objective lens undeviated to be incident upon the lateral oblique mirror which itself is at an angle of 47° with respect to said center plane of symmetry. The angle of incidence of said chief ray at said lateral oblique mirror is thus 47° as is the angle of reflection, measured with respect to a normal to said mirror at the point of reflection. Said reflected chief ray at said lateral oblique mirror is thus inclined at an angle of 4° with respect to said center plane of symmetry as is the inclination of the optical axis of the ocular lens of said telescope which coincides with the reflected chief ray from said lateral oblique mirror.

Of importance is the fact that the extended optical axis and axial chief ray of the objective lens and those of the ocular lens intersect and are reflections of each other at the lateral oblique front surface mirror. Two lenses having a common straight line optical axis are said to be coaxial. In this specification I have extended the concept of coaxiality to include those situations in which a mirror is interposed between two lenses such that the optical axis of one of the lenses intersects the optical axis of the other at said mirror and the two axes and the normal to the mirror surface at their point of intersection all lie in the same plane, with the angle between the optical axis of the first of said lenses and the normal to the surface and that between the optical axis of the second of said lenses and the normal to the surface being equal. This, in essence, is the law of reflection substituting optical axes for light rays. The two lenses are still said to be coaxial and the two lenses and the interposed mirror comprise the coaxial movable telescope unit of the indirect ophthalmoscope of this invention.

Although 47° is a very useful angle between the lateral oblique mirrors and the center plane of symmetry, said angle may be less than 47° or greater than 47°, approximately 46° or 48°, for example, in accordance with a working distance for indirect ophthalmoscopy somewhat less or greater respectively than the usual working distance of 16 inches and in accordance with the interpupillary distance of the observer, a large interpupillary distance requiring a larger angle and a small interpupillary distance requiring a smaller angle.

In adjusting the indirect ophthalmoscope of this invention for the interpupillary distance of the observer, the movement of said unit must be along ways perpendicular to said center plane of symmetry to maintain coincidence of the optical axis of said unit and said chief ray reflected from said medial oblique mirror. During such an adjustment the inclination of said lateral oblique mirror remains at 47° with respect to said center plane of symmetry. Also any adjustment of the ocular lens for focusing of the telescope is in the axial direction of the ocular lens of the telescope, thereby maintaining coaxiality of the unit.

FIG. 8, drawn to scale, shows in detail for one-half of said first embodiment as shown in FIG. 6, of the indirect ophthalmoscope of this invention, the positioning and inclination of the positive objective lens and the negative ocular lens with respect to the lateral flat oblique front surface mirror. The two lenses and said lateral oblique mirror comprise the fixed unit which can be moved transversely along ways without the necessity for change in the telescopic adjustment when adjusting the ophthalmoscope for interpupillary distance by moving said unit toward and away from its respective medial flat oblique front surface mirror. The negative ocular lens is held in an axially adjustable mounting with a screw thread for fine adjustment in the axial direction. The image of the aerial image of the fundus of the eye as seen through this embodiment of the invention remains inverted.

FIG. 9, drawn to scale, is similar to FIG. 8 with the exception that the telescope incorporated in said fixed unit is an astronomical telescope wherein the ocular lens is a strong positive lens. The relative fixed positions of the objective and ocular lenses with respect to the lateral oblique mirror are shown. There is adequate distance between the front surface of the objective lens and the medial oblique mirror to allow for adjustment of said ophthalmoscope for observers with small interpupillary distances. The image of the aerial image of the fundus as seen by an observer through this embodiment of the indirect ophthalmoscope of this invention is upright.

The objective lens of said incorporated telescope is a strong positive lens of homogeneous transparent optical glass or plastic. The objective lens of the astronomical telescope is considerably stronger than that of the Galilean telescope. I have included spherical objective and ocular lenses as elements of the telescope of this invention; however, such lenses when very strong as in the astronomical telescope, can produce considerable aberrations in the image formed through them and it is necessary with said strong lenses as in the incorporated astronomical telescope, that the lens elements of the telescope be aspheric, with one or both surfaces of the objective lens being aspheric and one or both surfaces of the ocular lens also being aspheric, if aberrations are to be reduced to a minimum. The use of aspheric objective lenses, especially if both front and back surfaces are aspheric, insures that a homocentric bundle of light rays originating in the aerial image of the fundus, rendered parallel by said columnating lens, and reflected from said medial oblique mirror and incident upon said objective lens, will be focused toward an essentially aberration-free image at the secondary focal plane of said objective lens. It is of course necessary that the aerial image of the fundus is itself essentially flat and aberration-free and the use of my double aspheric indirect ophthalmoscopy lens as described in the specification of my copending patent application, Lens For Indirect Ophthalmoscopy, Ser. No. 437,279, produces such an aerial image. Divergent homocentric bundles of light rays from said inverted aerial image of the fundus are incident upon the columnating lens of the indirect ophthalmoscope of this invention which refracts said bundles to homocentric bundles of parallel light rays directed towards the medial oblique front surface mirror of said ophthalmoscope which in turn reflects the homocentric bundles of parallel light rays to the front aspheric surface of the objective lens.

When the incorporated telescope is an astronomical telescope, the homocentric bundles of light rays emerging from the back aspheric surface of said objective lens are incident upon the lateral oblique front surface mirror and reflected to a real reinverted (upright) aerial image of the aerial image of the fundus in the secondary focal plane of said objective lens which is also the primary focal plane of the ocular lens of said astronomical telescope. Said reinverted aerial image then becomes the object for the ocular lens of said telescope. The ocular lens is so designed with both front and back surfaces aspheric that diverging homocentric bundles of light rays from points in said object plane, after refraction by said ocular lens, proceed as homocentric bundles of parallel light rays, with the chief ray of each bundle proceeding towards the back focus of said ocular lens. When the observer's eye is positioned with the center of its entrance pupil at the back focus of the ocular lens of said telescope, the image of the fundus as seen by means of the indirect ophthalmoscope of this invention will be enlarged and upright.

In the binocular indirect ophthalmoscope of this invention incorporating the astronomical telescope, the dioptric power of the objective lens may be as low as 40 diopters or as high as 80 diopters, while the dioptric power of the ocular lens may likewise be a value between 40 and 80 diopters. An objective lens of 60 diopters in combination with an ocular lens of 70 diopters is well suited for the incorporated astronomical telescope: it permits a full range of adjustability for the interpupillary distance of the observer, and because of the high dioptric powers of both the objective and the ocular lenses, the head-borne indirect ophthalmoscope of this invention can be made compact and used close to the observer's eyes.

The magnification produced by the incorporated astronomical telescope is a function of the ratio of the dioptric power of the ocular lens divided by the dioptric power of the objective lens. Additional magnification is provided by the positive aspheric columnating lens. For example, if the power of the columnating lens is 3.37 diopters, the magnification produced by it is 1.25, and if the power of the objective lens of the telescope is 60 diopters and that of the ocular lens is 70 diopters, the magnification of said telescope is 1.167. The total magnification of the indirect ophthalmoscope of this invention is then $1.25 \times 1.167 = 1.46$.

It is understood that the dioptric powers of the objective and ocular lenses of the astronomical telescope may be other than 60 and 70 diopters respectively and still be completely compatible with the dimensions and concepts of the indirect ophthalmoscope of this invention, thereby obtaining other magnifications. As an example, the objective lens of said telescope may have a dioptric power of 55 and the ocular lens may have a dioptric power of 75, and the columnating lens may be kept at a dioptric power of 3.37 whereby the magnification of the primary aerial image of the fundus of the eye will be $1.36 \times 1.25 = 1.70$.

If the dioptric power of both the objective lens and the ocular lens of the incorporated astronomical telescope are the same, magnification produced by means of the telescope will be 1.00 and the total magnification will be that produced by the columnating lens only, 1.25, with the power of the columnating lens still at 3.37 diopters. The image as seen by the observer will be enlarged and upright.

When the incorporated telescope is a Galilean telescope (see FIG. 8), the homocentric bundles of converging light rays emerging from the back surface of the objective lens of the telescope are incident upon the lateral oblique flat front surface mirror, and after reflection by said mirror are directed toward the repositioned secondary focal plane of said objective lens. The negative ocular lens is coaxial with the redirected optical axis of said objective lens and is interposed between the lateral oblique mirror and said secondary focus of the objective lens, with its primary focal plane coinciding with the secondary focal plane of said objective lens. The image seen by the observer is inverted and enlarged. Magnification of said Galilean telescope is equal to the ratio of the dioptric power of the ocular lens divided by the dioptric power of the objective lens. As an example, if the power of the objective lens is 20 diopters and that of the ocular lens is 30 diopters, magnification is then 1.50. If the magnification due to the columnating lens is 1.25, then the total magnification is then $1.50 \times 1.25 = 1.88$. As a second example, if the dioptric powers of the objective and ocular lenses of the included Galilean telescope are 25 and 35 diopters respectively, then magnification by the telescope is 1.4. If the magnification due to the columnating lens is 1.25, then the total magnification is $1.4 \times 1.25 = 1.75$.

Figures 10, 10A, 11:
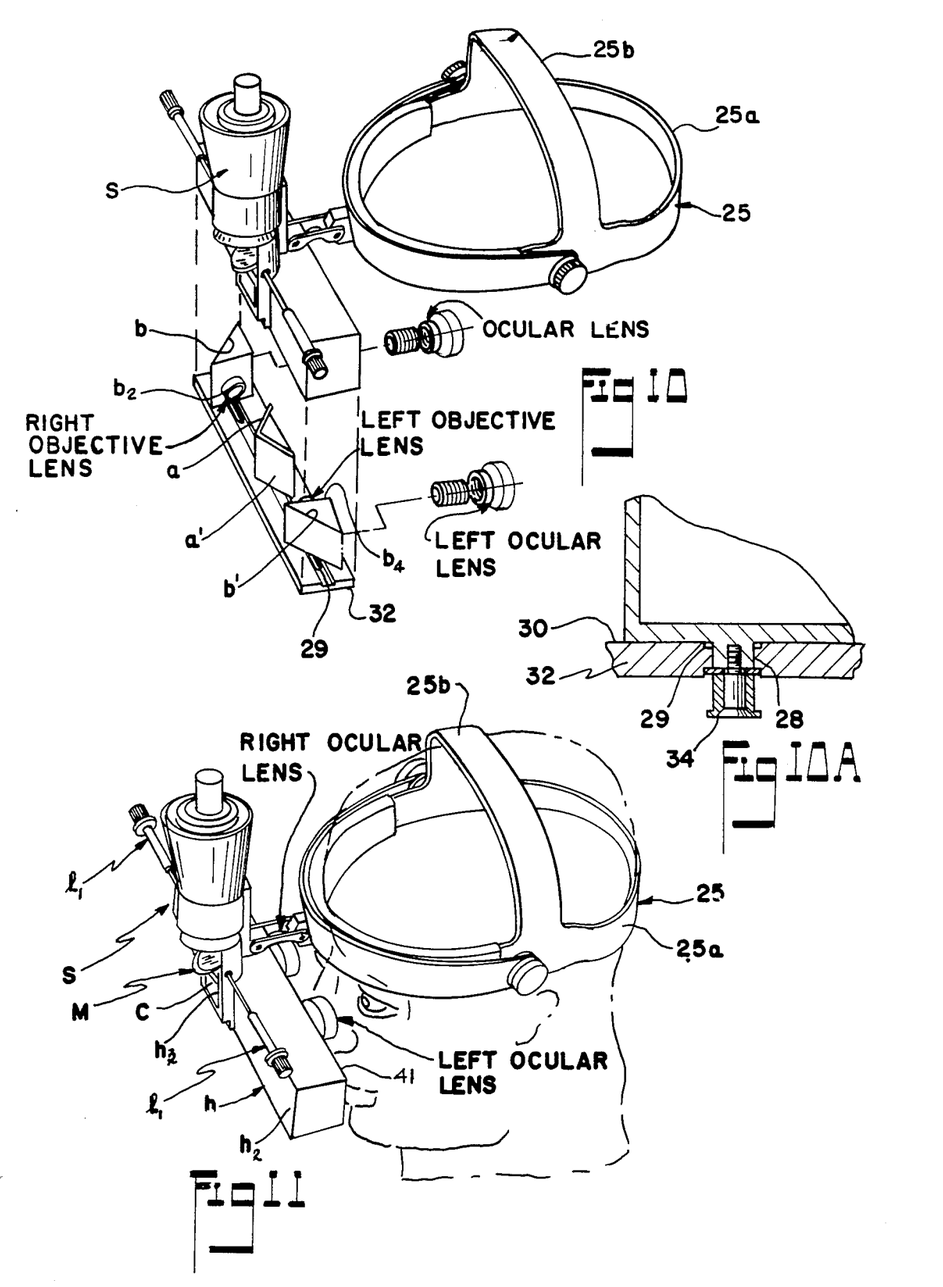

In FIGS. 10 and 11, I have shown an ophthalmoscope unit which incorporates the lens and mirror assembly of the present invention as set forth herein in FIGS. 4–9.

Specifically as seen in FIGS. 10, 10A and 11, a strap assembly 25 comprises a peripheral head part 25a and an upwardly projecting crown part 25b adapted to lie around and over the user's head as best seen in FIG. 11.

A suitable light source S as referred to in FIG. 1 is mounted to the top wall of an elongated tubular housing h which is square in cross section.

As seen in FIGS. 10 and 11, mirror M is rotationally adjustable about its axis by finger lever $l_1$ to position the light beam from mirror M to condensing lens $C_2$ held by the observer.

The observing lens and mirror system of the ophthalmoscope is disposed within the housing h so as interact with the light source S and its associated light reflecting mirror M.

The observing lens and mirror system incorporates the system as shown in FIGS. 6–9 and includes medial oblique flat front surface mirrors a and a', lateral front surface mirrors b and b', objective lens, and ocular lens as a unit "u".

As best seen in FIGS. 10 and 10A each lateral front surface mirror b and b' is fixedly mounted on a boss 28 disposed within an elongated recess 29 which is formed on the upper surface 30 of rectangular mounting plate 32.

The boss 28 projects through a slot 36 formed in the recess 29 and threadedly connects on its underside with a suitable fastener 34.

With this assembly, each boss 28 and mounted lateral mirror b and b' can be slidably moved as a unit transversely toward and away from each other to adjust for the inter-pupillary distance of the observer's eyes.

The front wall $h_2$ of the housing $h_2$ is formed centrally with a window $h_3$ in which the columnating lens C as seen in FIG. 6 is mounted so as to be directly in front of front surface mirrors a and a'.

The left and right ocular lenses are mounted in eyepiece units p and p' which in turn are mounted to the back wall of the lateral oblique front surface mirrors b and b' respectively so as to be movable with said mirrors b and b' and thereby position said eyepieces at the interpupillary distance of the observer.

As best seen in FIG. 10, the right objective lens is attached to wall $b_2$ of the lateral oblique front surface mirror b, and in like manner, the left objective lens is attached to wall $b_4$ of the lateral oblique front surface mirror b'.

With this ophthalmoscope, the observer places the same onto his head, as seen in FIG. 11, and connects the light source to a suitable source of electrical current. The observer then holds the condensing image forming lens $C_2$, as seen in FIG. 6, in front of the eye to be examined whereby the light beam from the mirror M is directed through said lens $C_2$ to illuminate the eye being examined.

The reflected light from the examined eye is then passed back through the pupil to the condensing lens $C_2$ to form aerial image i.

The light rays from image i proceed to condensing lens C and are refracted to medial oblique mirrors a and a' where they are reflected to the left and right objective lenses.

Said light rays are then refracted by said objective lenses to lateral oblique mirrors b and b' where they are then reflected to left and right ocular lenses and then refracted to the observer's eyes e and e'.

In both the astronomical and Galilean telescope of this invention, the lenses are made of homogeneous transparent glass or plastic of a given index of refraction. For example, the lenses are generally made of ophthalmic crown glass having an index of refraction of 1.523. Ophthalmic crown glass has relatively low chromatic dispersion. Also, the light emitted from the eye when white light is used as the light source in indirect ophthalmoscopy, is primarily limited to the yellow to red portions of the visible spectrum so that the aerial image of the fundus of the eye appears orange-red. The limitation of the range of spectral wave lengths of emitted light mainly to the orange-red portion of the visible spectrum practially eliminates chromatic blurring of the image of the fundus as seen by means of the indirect ophthalmoscope of this invention. In the Galilean telescope used in this invention, chromatic aberration even of a small amount can be reduced by the appropriate combination of indices of refraction and Nu values of each of the two elements of the telescope.

The surfaces of all lenses in the ophthalmoscope of this invention are multicoated to increase light transmission through each surface to better than 99%, thereby reducing the loss of light by reflection at each lens surface.

I claim:

1. A head-borne binocular indirect ophthalmoscope containing a single centered light source slightly above the usually horizontal level of the bilateral symmetrical observing system of the ophthalmoscope, for directing a beam of light toward a hand-held indirect ophthalmoscopy lens, a low powered columnating lens located symmetrically in front of medial right and left oblique flat front surface mirrors which meet at an angle of 90° in a central usually vertical edge, each of said mirrors at an angle of 45° to the usually vertical center plane of symmetry of said ophthalmoscope, a pair of identical strong positive aspheric right and left telescope objective lenses with the front surface of each objective lens facing obliquely its respective medial oblique mirror, the optical axis of each of said objective lenses intersecting its respective medial oblique mirror at an angle of 45° with respect to a normal to the mirror, a second pair of lateral right and left flat oblique mirrors in oblique relation to the back surface of each objective lens, each of said lateral oblique mirrors at an angle of substantially 47° with respect to said center plane of symmetry of said ophthalmoscope the optical axes, and the axial chief rays along said optical axes, of said right and left objective lenses being coaxial and each intersecting its lateral oblique mirror at an angle of incidence of substantially 47° to then be reflected at an angle of reflection of substantially 47° so that each redirected optical axis of each objective lens is substantially 94° its original direction, to then become the optical axis and axial chief ray of each of the identical right and left ocular lenses of said telescopes, each lateral oblique mirror and its associated objective and ocular lenses forming a unit with the objective and ocular lenses fixed in coaxial position with respect to said mirror so that the optical axes of said objective and ocular lenses of said unit always intersect at a point on said lateral oblique mirror at an angle of substantially 94°, the secondary focus of each of said objective lenses coinciding with the primary focuses of its corresponding ocular lens.

2. An indirect ophthalmoscope as in claim 1 wherein ocular lens of said unit is a positive lens forming with the positive objective lens an astronomical telescope.

3. An indirect ophthalmoscope as in claim 1 wherein the ocular lens of said unit is a negative lens forming with the positive objective lens a Galilean telescope.

4. A single element columnation lens as in claim 1 whose optical axis lies in the center plane of symmetry having an anterior vertex power within a range from +2.00 to +4.50 diopters.

5. An indirect ophthalmoscope as in claim 1 with means for adjusting the ocular lenses axially for accurate adjustment of the telescope.

6. An indirect ophthalmoscope as in claim 1 with means for adjustment of the units towards and away from each other to accommodate the interpupillary distance of the observer.

7. An indirect ophthalmoscope as in claim 1 wherein said objective and ocular lenses have spherical and plane surfaces.

8. An indirect ophthalmoscope as in claim 1 wherein one surface of the objective lens is aspheric and the ocular lens is spherical.

9. An indirect ophthalmoscope as in claim 1 wherein the objective and ocular lenses are aspheric with each lens having at least one aspheric surface.

10. An indirect ophthalmoscope as in claim 1 wherein the objective lens has two aspheric surfaces and the ocular lens is spherical.

11. An indirect ophthalmoscope as in claim 1 wherein the objective lens has two aspheric surfaces and the ocular lens as one aspheric surface.

12. An indirect ophthalmoscope as in claim 1 wherein the objective lens has two aspheric surfaces and the ocular lens has two aspheric surfaces.

13. An indirect ophthalmoscope as in claims 1 and 3 wherein the objective lens is of crown glass of low chromatic dispersion, and the ocular lens is of glass of a higher index to refraction and of a different relative chromatic dispersion to compensate for chromatic aberration of the telescope units.

* * * * *